United States Patent [19]

Usala

[11] Patent Number: 5,236,703
[45] Date of Patent: Aug. 17, 1993

[54] POLYMERIC SUBSTRATES CONTAINING POVIDONE-IODINE AS A CONTROL RELEASE BIOLOGICALLY ACTIVE AGENT

[75] Inventor: Anton-Lewis Usala, South Euclid, Ohio

[73] Assignee: Virex Inc., Cleveland, Ohio

[21] Appl. No.: 382,857

[22] Filed: Jul. 20, 1989

Related U.S. Application Data

[63] Continuation-in-part of Ser. No. 272,408, Jan. 8, 1989, abandoned, which is a continuation-in-part of Ser. No. 87,604, Aug. 20, 1987, abandoned.

[51] Int. Cl.$^5$ .................... A61K 33/18; A61K 31/79; A61L 29/00; A61L 31/00; A61L 17/00; A61L 25/00; A61M 25/00

[52] U.S. Cl. .................... 424/78.36; 424/78.31; 424/402; 424/423; 424/430; 424/485; 424/486; 424/487; 424/411; 424/667; 424/672; 424/175.1; 514/782; 514/772.3; 514/772.4; 514/772.6; 523/122; 128/844; 128/849; 604/93; 604/358; 606/228; 2/159; 428/343; 525/182

[58] Field of Search .................... 424/81, 28, 80, 83, 424/402, 423, 430, 485, 486, 667, 672; 514/782, 789, 950, 964; 523/111, 113

[56] References Cited

U.S. PATENT DOCUMENTS

| | | | |
|---|---|---|---|
| 4,310,509 | 1/1982 | Berglund et al. | 424/78 |
| 4,500,339 | 2/1985 | Young et al. | 71/67 |
| 4,538,603 | 9/1985 | Pawelchak et al. | 424/449 |
| 4,769,013 | 9/1988 | Lorenz et al. | 424/80 |
| 4,793,337 | 12/1988 | Freeman et al. | 424/284 |

Primary Examiner—Thurman K. Page
Assistant Examiner—E. J. Webman
Attorney, Agent, or Firm—Peter D. Sachtjen

[57] ABSTRACT

A polymeric substrate such as rubber or latex incorporates povidone-iodine as a control release biologically active agent.

10 Claims, 3 Drawing Sheets

POLYMERIC SUBSTRATES CONTAINING POVIDONE-IODINE AS A CONTROL RELEASE BIOLOGICALLY ACTIVE AGENT

RELATED APPLICATIONS

This application is a continuation in part of copending U.S. patent application Ser. No. 07/272,408 filed on Jan. 8, 1989 now abandoned which is a continuation in part of U.S. patent application Ser. No. 087,604, filed on Aug. 20, 1987 and now abandoned.

FIELD OF INVENTION

This invention relates to polymeric healthcare articles, for example surgical and medical goods and equipment, which are useful in preventing the contamination, transmission and penetration of various diseases and/or infections to humans and animals and to the process of preparing same. More particularly, this invention relates to rubber articles, for example films, coatings, and like substrates, comprising a rubber polymer incorporating as a control release biologically active agent, the proven antimicrobial povidone-iodine, when the substrate is exposed to a polar liquid so as to prevent contamination by a viable pathogen, such as a virus, bacteria, or fungus. This invention can be used to prepare various healthcare articles such as medical gloves (examination and surgical), condoms, and durable and disposable medical equipment, such as catheters, to prevent contamination, transmission and penetration by various diseases and/or infections such as hepatitus, venereal diseases, AIDS, and the like.

Viruses, in particular, have limited life outside the human body, but are quite virulent once inside the human body. Other viruses, such as AIDS, hepatitis and the herpes simplex virus, for example, are relatively easy to kill outside the body, but once inside become quite difficult to control and may be fatal. Thus control of these pathogens is an ongoing healthcare objective. In comparison to the general population, people involved in health care incur a higher probability of encountering diseases because they are in contact with the diseases on a daily basis while handling body fluids such as blood, urine, mucous secretions and the like. Each day, physicians, nurses, other medical personnel handle and are exposed to these body fluids, with the only protection being barrier prophylactic articles, such as gloves, gowns and masks. Some of these articles may be porous and therefore allow some pathogens to penetrate through to the skin and transmitted to the individual through abrasions, scratches and wounds. Other barrier articles such as condoms are suggested for use by the general public to prevent the transmission of venereal disease or infection by the pathogens. While these prophylactic articles are comparatively effective, they are not guaranteed to prevent the transmission of the above mentioned bacteria, viruses or funguses.

In healthcare facilities, the transmission, penetration and contamination can occur in many ways. Gloves, for example, are used by various medical personnel. Surgeons wearing initially sterilized gloves, encounter patient fluids during surgery which may contain pathogens. Should defects exist or be developed in the glove, pathways therethrough can bring the pathogens into direct contact with the surgeon's hand and create the potential for infection at any open wound or abrasion. Similarly, if a glove and consequently the surgeon's hand are cut during treatment, pathogens may be drawn by the instrument into the cut thereby creating a potential infection site. All medical personnel involved in patient treatment are likewise exposed to pathogenic fluids. In addition to penetration problems of the type referenced above, there is also the clear possibility that the glove may directly contact infected fluids and accordingly may be a source of contamination for the wearer, other personnel or patients or surrounding equipment. Other durable and disposable healthcare goods, even if packaged sterile, may become contaminated during patient treatment thereby creating infection sites and transmission paths for further infection of the patient. Patients treated with interdwelling catheters, in particular urinary catheters, commonly develop infections which can spread to other tissue and organs. For general healthcare, latex condoms are regarded as the best barrier protection against sexually transmitted diseases. The thin wall sections of condoms are likewise prone to defects, ruptures or tears, all of which destroy the barrier protection thereby creating pathways for the transmission of infected body fluids.

Polymeric materials are commonly used for the above and other healthcare goods. Latex is the material of choice for barrier articles in many medical and health applications, both durable and disposable. Natural latex, in particular, dominates other materials for gloves and condoms and is a significant manufacturing material for catheters. The unique combination of high tensile strength and elasticity, low modulus, and the ability to form coherent wet and dry conformal films makes natural latex ideally suited for the high speed manufacture of dip formed healthcare articles. Unlike other polymeric materials, conformal dip coating provides finished articles of desired shape, without seams, in accurately controllable thicknesses. Compared to alternative polymers, such as thermoplastics, latex films have significant structural and functional advantages. Additionally, the superior elongation permits manufacture of articles which can accommodate large size ranges of body parts while maintaining tight conformal contact. The ability to form extremely thin walls, provides superior tactility for the user.

Notwithstanding the above structural and functional advantages, latex is a difficult material with which to manufacture articles. Natural latex is a complex colloidal system which contains high molecular weight cis-polyisopropene polymer, proteins, lipids, phosphlipids, sugars, inorganic salts, resins and other chemical compositions. The organic components of natural latex, derived from trees in tropical, humid climates, may have been exposed to various bacteria, enzymes, and oxygen. Accordingly, preservatives and controlled processing are required to inhibit adverse reactions. Certain components, such as salts, must be removed before manufacture. Further chemicals are added for mechanical stability, chemical stability, curing and vulcanization. Lastly, antioxidants, antiozanants, sequestrants, plasticizers, colorants and fillers are added to obtain desirable physical properties and extended properties for the finished articles. The resultant formulation is accordingly extremely complex and oftentimes contains 40 or more distinct chemicals.

Polymeric materials, such as plastics and rubber, are used in the manufacture of medical equipment, and the desirability of self-sterilizing polymers therefor has become recognized. There have been attempts to combine such polymeric materials with antibacterial agents for the manufacture of various medical goods and equipment, such a gloves, condoms and the like. However, the aforementioned complexity of the latex formulation has limited their incorporation into dipped or coated latex health care goods.

For example, Laurin et. al, U.S. Pat. No. 4,603,152 discloses a catheter incorporating compounds of physiological, antimicrobial metals in various polymers, including latex. Release of the metals requires interrelation of metal particle size and the dielectric constant of the resin. The composition also requires thorough mixing to obtain an even dispersion of the particles. LeVeen et al U.S. Pat. No. 4,381,380 discloses a post formation treatment with iodine solutions to incorporate a releasable antimicrobial into narrowly defined sparingly cross linked polyurethanes. Wepsic, U.S. Pat. No. 3,598,127, discloses a polysiloxane rubber incorporating an antibacterial which diffuses through the substrate and is incorporated through post formation absorption or physical entrapment in an adjacent component. James et. al., U.S. Pat. No. 4,499,154, discloses the post formation bonding to rubber articles of a lubricating hydrogel incorporating a bactericidal cationic surfactant. Vorhauer et. al., U.S. Pat. No. 4,393,871, discloses the incorporation of drugs into a polyurethane prepolymer which is which is foamed and utilized as a vaginal device. European Patent Application No. 88306760.5 published on Jan. 25, 1989 discloses a medical glove which is post formation treated with an antimicrobial agent with an antimicrobial slurry polyurethane or polyethylene incorporating an antimicrobial.

It is apparent that none of the foregoing approaches provides a dip formed latex substrate incorporating a releasable antimicrobial and applied in an operation compatible with existing manufacture.

BRIEF SUMMARY OF THE INVENTION

In accordance with this invention, the medical goods and equipment can be manufactured from a latex capable of control releasing a biologically active agent when in contact with a polar solution such as blood or mucous membrane tissue, body liquids and the like. These goods can be rendered self-sterilizing by coating a film of the latex on the goods or by manufacturing the goods from a latex material incorporating a releasable biologically active agent.

More particularly, latex substrates incorporate povidone-iodine, both as a control releasable antimicrobial agent and also as a vulcanizing or cross linking agent. The film forming process for making such a latex substrate is compatible with existing manufacturing processes. This process can be utilized for making the entire article substrate or for making a substrate coating on the article. Moreover, the agent may be provided in discrete layers and, as such, provide select zones or layers of antimicrobial protection for such articles. Articles so formed are capable of control-releasing povidone-iodine when in contact with a polar liquid to prevent contamination, transmission or penetration by pathogens. Examples of such latex articles are gloves, condoms, catheters, tubings, and other elastomeric materials used for a variety of medical or health related applications.

According to the present invention, latex substrates, in single or multiple layers, incorporate povidone-iodine, which is controlled in chemical bonding with the latex, so as to be releasable upon contact with polar liquids. Generally, the release of povidone-iodine is achieved by controlled processing of a mixture of povidone iodine and latex concentrate so as to retain the povidone-iodine in the substrate through secondary forces or van der Waals bonds, to the predetermined exclusion of chemical bonding with the latex. Such controlled processing provides controlled release of the agent, both as to concentration and duration, in accordance with the requirements of the environment to which the substrate is applied. The controlled processing, without limitation, includes controlled mixing and viscosity, emulsification, heating time temperature and rate. These process parameters can be controlled, individually or in combination, to achieve the desired predetermined exclusion of chemical bonding between the antimicrobial and the latex.

More specifically, in the manufacture of surgical gloves, the latex substrate comprises at least one layer of the substrate which contains a sufficient amount of the biologically active agent to effectively kill a broad range of pathogens. A multilayer article may have different amounts of the agent in each layer, and accordingly different release rates for each layer.

The latex substrates of the present invention can be used for making various specialty goods. For instance, gloves can be made with discrete control release layers having benefit in many healthcare applications. Medical personnel handling potentially infected body fluids over a prolonged period of time could be provided with a high dosage, fast release outer layer and a slow release low concentration inner layer. In the event of contact with such body fluids, the release at the outer layer would have a cidal effect and prevent touch contamination by such injected fluids. The inner layer would be released by wearer perspiration and provide protection against penetration of the fluids. A dentist's glove would benefit from a design with minimal release from the outer layer in contact with the patient while providing the aforementioned bathing layer at the inner layer/hand interface. In such instances, the outer layer may be formed by conventional formulations and techniques. Alternatively, the outer layer may be formed of the antimicrobial latex utilizing the above mentioned process controls. A layer with such characteristics can be effectively formed by slow, low temperature drying of the outer layer. Substrates formed in this manner show no ascertainable release of povidone-iodine when exposed polar solutions. Similar release rates can be obtained by using aged mixtures in which substantially all the povidone-iodine is chemically bound with the latex. Such a layer, while not releasing the povidone-iodine upon contact with polar solutions, will nonetheless prevent a nidus of infection from-developing in storage or in use.

For the very small group of people having a mild allergic reaction to povidone iodine, the above glove construction could be reversed to place the no release substrate on the inner surface with the desired release rate on the outer surface in accordance with the necessary processing parameters.

BRIEF DESCRIPTION OF THE DRAWINGS.

The above and other objects and advantages of the present invention will become apparent upon reading the following description of the preferred embodiments taken in conjunction with the accompanying drawings in which.

DETAILED DESCRIPTION OF THE PREFERRED EMBODIMENTS

Figure 3:
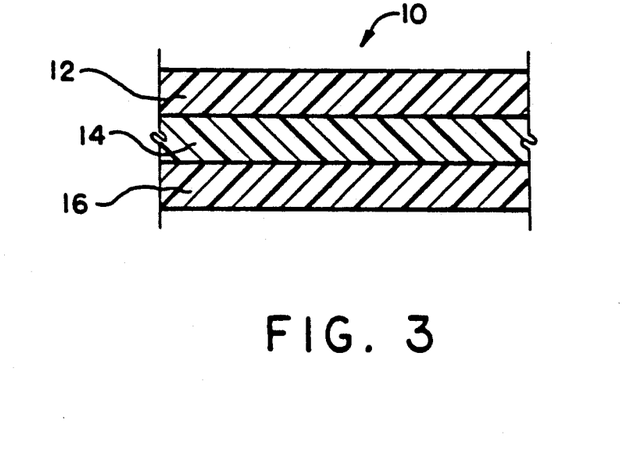
FIG. 3 is a fragmentary cross sectional view of a multilayer polymeric substrate in accordance with the present invention.

Referring to the drawings for the purpose of describing the preferred embodiments only, FIG. 3 shows a multilayered polymeric substrate 10 comprising an outer layer 12, an inner layer 14, and a middle layer 16. The layers each comprise a polymeric film having dispersed therewithin an antimicrobial agent which is control releasable upon contact with a polar solution to thereby prevent the penetration of a pathogen through the film. As described in greater detail below, the agent is dispersed in the polymer layers under controlled processing conditions limiting the chemical bonding therebetween. The amount of biologically active agent dispersed in the polymeric film may range up to about 25% by weight of the film, and preferably in amounts ranging from about 0.01 to 10% by weight of the polymeric film. The agent is added to the polymer in the form of concentrated solution, typically water solutions containing up to 25% by weight of agent.

Each layer may contain a different amount of the control release biologically active agent in comparison to the other layers. As described in greater detail below, each layer is formed through controlled processing including, without limitation, controlled mixing and holding, controlled viscosity, and controlled heating conditions including temperature, time and rate.

The various articles that can be prepared from the polymeric substrates include surgical covers or gloves, tubes, sponges, pads, catheters, sutures, surgical tape, condoms and the like.

Particularly effective for the foregoing is the incorporation of povidone iodine into natural latex as a preferred embodiment and the description will proceed with particular reference thereto. However, it will be apparent that other like polymers may be used with the povidone-iodine. For instance, film-forming polymeric barrier material containing a double bond in the polymer chain and capable of being vulcanized or cross linked such as natural or synthetic rubber, rubber latexes, silicone rubber, butyl rubbers, and more specifically, various synthetic rubbers such as the polyisoprenes, butadiene-styrene polymers, and neoprene rubbers. Other polymeric film-forming materials include polymers prepared by homopolymerization or copolymerization of monomers with the monomers having at least one double bond such as ethylene, propylene, butene, pentene, isobutylenes, cyclobutene, cyclohexane, and the like, and also with monomers having at least two double bonds such as the dienes, butadiene, neoprene, pentadiene, and the like capable of being vulcanized or cross linked. Other elastomeric film forming polymers include copolymers derived from vinyl acetate, vinyl ethers, styrene, vinyl chlorides, acrylic derivatives such as acrylic and methacrylic acid, e.g. methyl methacrylate, with monomers having at least two double bonds capable of being vulcanized or cross linked.

More specifically, latex barrier articles such medical and surgical gloves are used by health care professional, in including doctors and nurses, to protect them against the transmission of a multitude of pathogens, for example viral, bacterial, and fungal pathogens which are encountered regularly while handling body fluids such as blood, urine, mucous secretions and the like. Thus, physicians, nurses, and various laboratory personnel who come into contact with these body fluids are in need of such article to provide protection against the transmission of these diseases.

While the latex gloves presently used by health care professions are very helpful in preventing the transmission of disease, some are porous and allow the pathogens to penetrate through to the skin of the wearer, and if there happens to be an open wound, or if the individual touches the mouth, that particular disease may be transmitted. Thus, even though the articles presently available are comparatively effective, they are not absolutely foolproof in preventing the transmission of a number of infectious pathogens.

The povidone-iodine is used in therapeutically effective amounts ranging up to about 25% by weight of the polymeric film, and preferably in amounts ranging from about 0.01 to 10% by weight of the polymeric film. Povidone-iodine is known to kill gram-positive and gram-negative bacteria, as wells as fungi, viruses, protozoa, and yeast. Povidone-iodine is approved by the FDA for skin, oral, and vaginal applications. Moreover, povidone-iodine may be utilized in latex substrate at relatively low concentrations without adversely affecting the physical properties of the substrate. Further, povidone-iodine has high efficacy in low concentrations and may be incorporated in relatively small amounts, ranging from about 0.01 to 5% by weight of substrate.

Natural latex, in particular, is noted for a combination of properties not possessed by the other polymeric substrates used for medical and health related goods. Its high tensile strength, excellent elasticity, low modulus and ability to form coherent wet and dry films leads to applications such as medical gloves, balloons, and condoms. However, natural latex is a complex colloidal system containing high molecular weight cis polyisoprene polymer, proteins, lipids, phospholipids, sugars, inorganic salts, resins and other chemical structures not presently identified. Accordingly, it bears little similarity to other thermoplastics particularly with regard to the addition of additives. Therefore the aforementioned attempts to provide antimicrobial properties through additives in specific polymers are far more uncertain in the case of latex.

It has been determined that the mere combination of latex and povidone-iodine will not produce releasable antimicrobial agents unless the processing occurs under controlled conditions. For instance, the resulting admixture must be carefully monitored with time. It has been found that the povidone-iodine will chemically bond with the latex over time such that the povidone-iodine is not releasable in the presence of polar solutions. Moreover, the bond is not convertible. Thus, if the mixture is used contemporaneously with mixing and processed under controlled heating conditions, the povidone-iodine is bound to the latex polymer with secondary or van der Waals bonds controlledly to the exclusion of the chemical or cross-link bonds such that the povidone-iodine is releasable from the substrate in the presence of a polar liquid. This is observable and controllable. After mixing the admixture has a distinctive brown color which gradually shifts to an ivory color over a 24 hour time period. The color shift also correlates to a change in viscosity. Further, the releasability can be controlled by control of the drying of the wet film. Air drying for instance provides a latex substrate with insignificant release of the povidone-iodine, indicated both by the color of the substrate, off white, and the lack of release in polar liquids. Moreover, the heating rate, heating time and temperature significantly affect the releasability of the povidone-iodine.

In accordance with this invention, the concentration or the amount and speed of release of the agent from the latex films can be controlled by regulating the degree of temperatures and rate of heating or drying of the film. The rate of heating and the temperature at which the mixture is heated, together with the concentration of the agent, are means of controlling the time release of said biological agent from the films.

EXAMPLE 1

Figure 2:
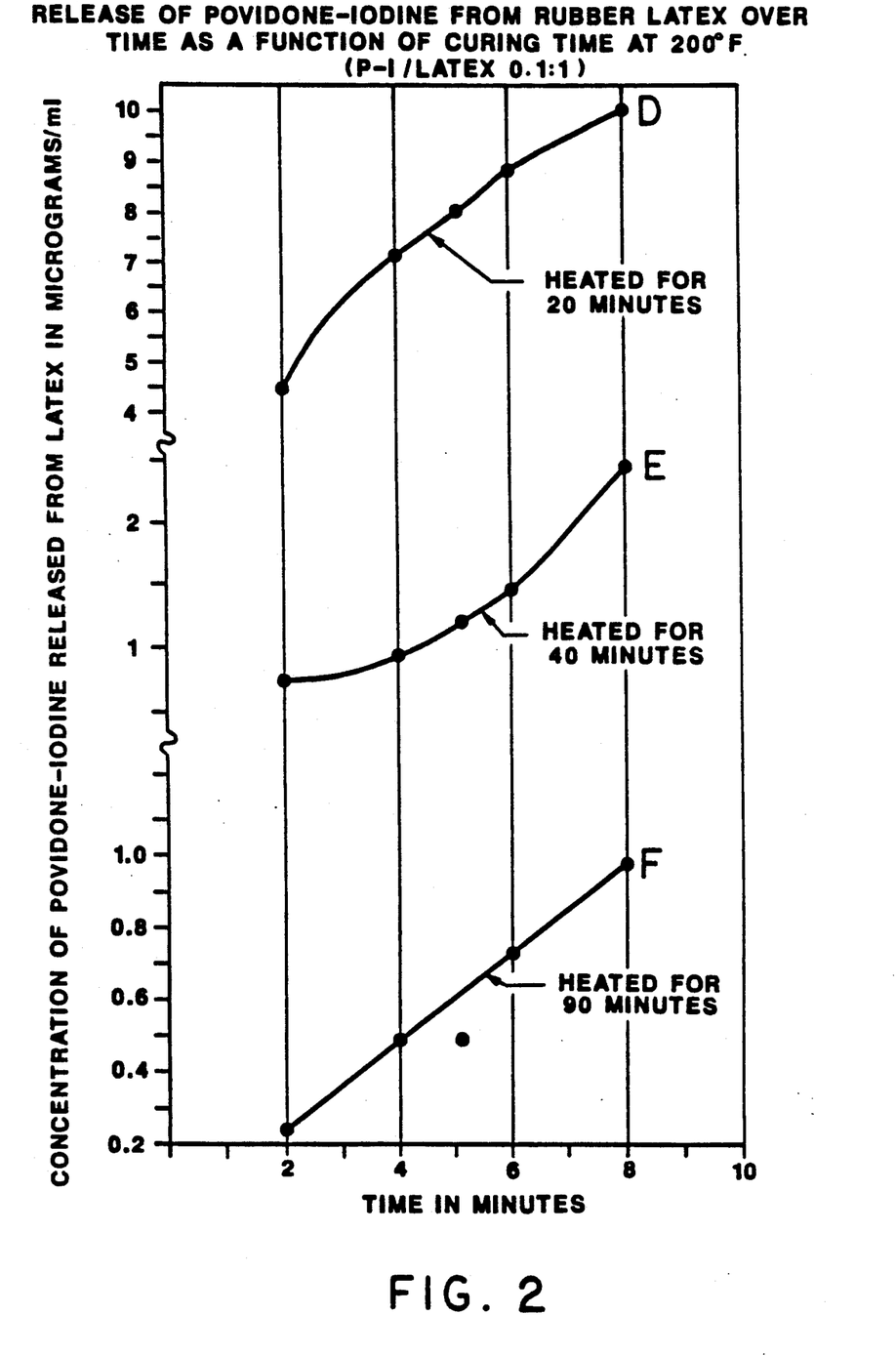
FIG. 2 are graphs showing release of povidone-iodine from latex as a function of curing time.

Two samples of a mixture of a low ammonia latex concentrate (Hartex 103 manufactured by Firestone) and a 10% aqueous solution of povidone iodine were prepared in equal volumes by weight with the povidone-iodine uniformly dispersed therewithin. One sample was held for a period of 24 hours and the change of color noted. Over this period the mixture changed from brownish color similar to the povidone-iodine solution to a whitish color similar to the latex concentrate.

EXAMPLE 2

Latex films were formed from each mixture sample prepared in accordance with Example 1. The films were dried at a temperature of 200° F. for 20 minutes. A towel, moistened with ordinary tap water, was applied to the film prepared from a fresh mixture. A brown color blotch characteristic of povidone-iodine was noted on the towel indicative of antimicrobial release. A damp towel was applied to film prepared from the 24 hour aged mixture. No color change was noted after removal.

As mentioned above, viscosity is another aspect of controlled processing of the mixture which can be used in providing the desired release of the povidone-iodine. Viscosity can be used to determine the amount of chemical bonding between the povidone iodine and the latex. Thus the condition of the mixture can be compared against standards to effect steady state dipping conditions and along with heating conditions and concentration the releasability of the povidone-iodine. An example illustrating the effect of holding time on viscosity follows.

EXAMPLE 3

Two mixtures were prepared in accordance with Example 1 above. Both samples were tested for viscosity on a Carri-Med CSL Rheometer available from Mitech Corporation of Twinsburg, Ohio. The aged sample had a higher viscosities at increasing shear rates than the fresh mixed sample indicating that povidone-iodine is incorporated within the polymer.

Thus, it is apparent that, in one aspect of controlled processing, the holding time as a function of color shift and/or viscosity can be used to control the release rate of the povidone-iodine. Moreover, these parameters also permit the makeup blending of fresh mixture into the dipping tanks to maintain predictable release control.

In accordance with a further aspect of the process for controlled release of the present invention, the concentration or the amount and speed of release of the antimicrobial agent from the latex film substrate can be controlled by regulating the drying temperature and rate of heating or drying. The rate of heating and the temperature at which the film is heated, together with the concentration of the agent, are means of controlling the time release of the agent from the film substrate upon contact with polar solutions as illustrated in Examples 4 through 6.

EXAMPLE 4

A natural rubber latex (Hartex 103, from Firestone Corporation) was mixed with different amounts of a 10% aqueous povidone-iodine solution. The latex was mixed with the solution at temperatures ranging from about 20° to 35° C. The povidone-iodine was added to the latex in amounts of 0.15:1, 0.1:1, and 0.05:1 by weight, and spread to films of about 20 mils. The films were subsequently heated for about 40 minutes at about 200° F. Slices of 140 milligrams were severed from the dried films and placed in 2 cc of normal saline water for specified periods of time. The povidone-iodine was found to be released into the saline water and the absorption measured at 378 nanometers, using a Beckman spectrophotometer. A standard curve was generated to ascertain the amount of povidone-iodine at a given absorption. Referring to the drawings, FIG. 1 shows the amount of povidone-iodine released from the latex films as a function of its concentration in the rubber latex. As the amounts increased from 0.05:1 to 0.1:1 and then to 0.15:1, the amount of the povidone-iodine released over a period of about 8 minutes into the water increased substantially from 0.6 (curve A) to about 2.0 (curve B), then to about 15.5 micrograms (curve C).

EXAMPLE 5

Polymeric films were prepared by the process set forth in Example 2. The mixture of 0.1:1 povidone iodine solution to rubber latex was heated for periods ranging from 20 minutes to 40 minutes and then to 90 minutes. As shown in FIG. 2, there is a significant decrease in the rate of release of the povidone-iodine as a function of heating, i.e., heating time, which can be regulated to control the amount of povidone-iodine to be released from the film. For example, the period of heating an agent and the latex mixture preferably is inversely proportional to the temperature. Thus, as the temperature increases, the amount of time needed to heat the latex mixture may decrease. As shown by FIG. 2, there is a significant decrease in the release of the povidone-iodine from the film as the heating time of the latex mixture is increased. Therefore, depending on the release rates needed for the particular article being manufactured, the temperature and the heating time can be appropriately controlled.

EXAMPLE 6

Three polymeric films were prepared from a mixture of the povidone-iodine and rubber latex in accordance with Example 2. The films were heated for 20, 40, and 90 minutes, respectively. The films were cut into 140 milligram samples. The samples were then placed in 2 ml of distilled water and the amount of povidone iodine released to the water from each sample was determined at time intervals by light absorption at 378 nanometers and compared to a standard povidone-iodine absorption curve at 378 nanometers. As illustrated in FIG. 2, the release of povidone-iodine from the film is an inverse function of the heating time for a given heating temperature. The sample (Curve D) heated for 20 minute released about 10 micrograms of the povidone-iodine from the rubber latex film after a period of about 8 minutes whereas the sample (Curve E) heated for 40 minutes released 2.5 micrograms and the sample heated for 90 minutes released 1.0 micrograms.

From the foregoing examples, it is apparent that concentration of the antimicrobial agent and the heating time of the latex film will permit control, in whole or in part, of the release of the povidone-iodine.

As mentioned above, the antimicrobial substrate may be incorporated into healthcare article in single or multiple layers, with each layer having a controllable release of the povidone-iodine. One embodiment is set forth in the following Example 7.

EXAMPLE 7

A mixture of 0.05:1 povidone-iodine (10% solution) to latex was cast and then heated for 90 minutes at temperatures not exceeding 200° F. An 0.15:1 mixture of the povidone-iodine 10% solution to latex was prepared and applied over a glove mold and heated for 40 minutes. Talc powder was applied to the exposed outer layer and the glove removed from the mold. 1 cc of normal saline solution was applied to the 0.15:1 mixture and to the 0.05:1 latex agent mixture on surfaces covering identical areas and allowed to sit for about 8 minutes. The higher concentration of 0.15:1 latex agent mixture (outer side) of the supernatant liquid showed a release of about 23 micrograms of povidone-iodine, while the lower concentration of 0.05:1 latex-agent mixture (inner side) gave a release of about 2 micrograms of povidone-iodine.

This multilayered glove with a slow release rate on the outer layer, a surgeon's glove, for example, has important biomedical implications in that the surgeon would benefit from the longer heat treatment for 90 minutes of the 0.05:1 mixture of latex on the inner layer of the glove which provides a more stable, slower release rate on the outside of the surgical glove. Should an inadvertent puncture of the glove occur, the surgeon's hand would be bathed in the povidone-iodine which would be carried into the wound. Since only very small amounts of free iodine are necessary to kill bacteria and various viruses, including the AIDS virus, this method of preparing surgical gloves provides effective protection against the transmission of diseases.

Figure 1:
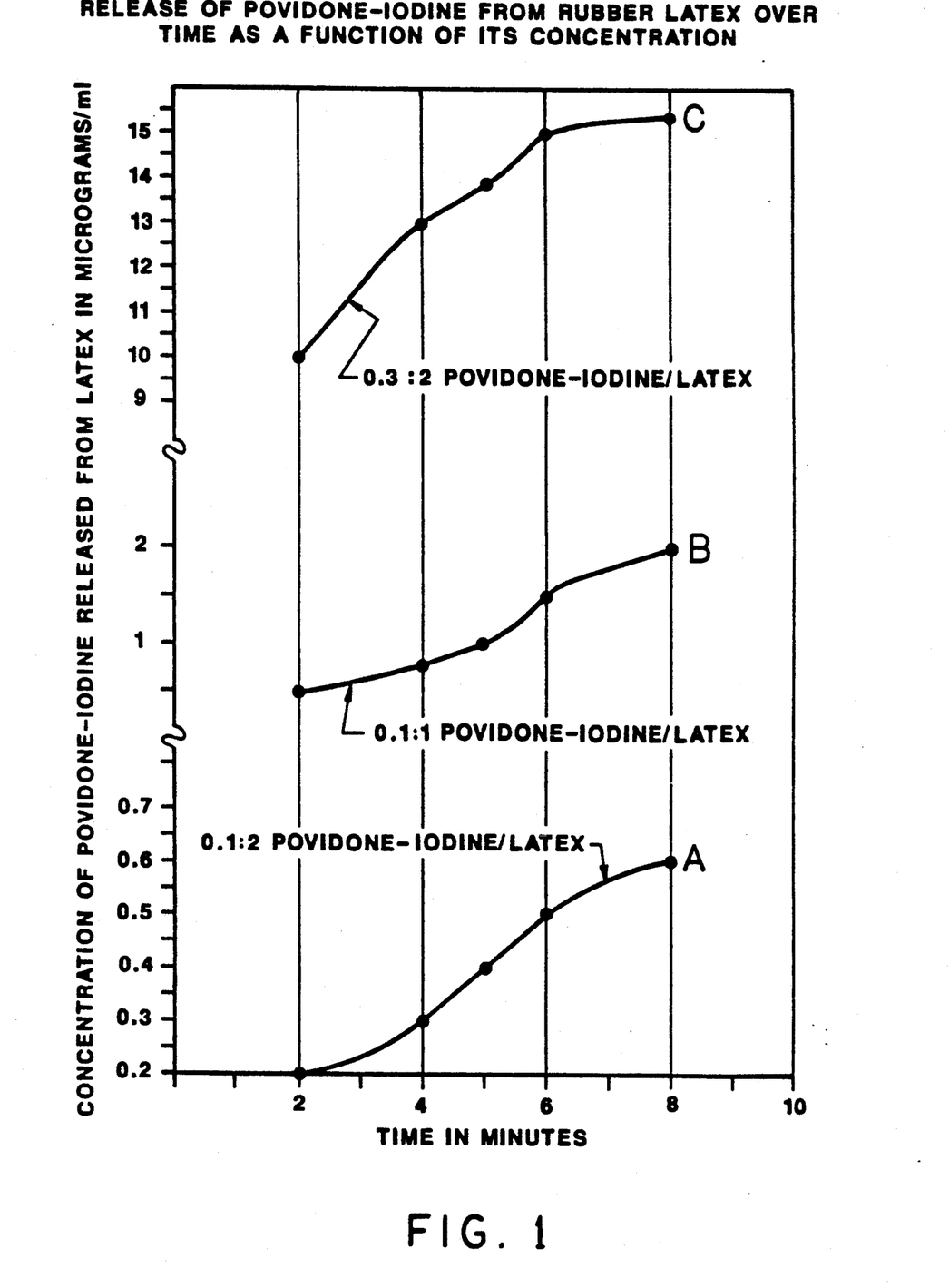
FIG. 1 are graphs showing release of povidone-iodine from latex as a function of concentration.

As shown in FIGS. 1 and 2, as the concentration of the povidone-iodine was increased from 0.05:1 to 0.1:1, the amount of the povidone iodine released from the latex film increased from about 0.6 micrograms as shown in Curve A to about 2.0 micrograms as shown in Curve B, and to about 15 micrograms as shown in Curve C as the amount of the povidone-iodine was increased from 0.05 to 0.1 and then to 0.15.

It was found further that as the period of time for heating the polymeric film-forming material decreased, for example, from about 90 minutes at 200° F. to 40 minutes and then to 20 minutes, the amount of povidone-iodine released from the latex increased from about 1.0 micrograms, as shown in Curve F to about 2.0 micrograms, as shown in Curve E, and ultimately to about 10.0 micrograms as shown in Curve D. Thus by varying the heating and/or curing time, e.g., from about 20 to 90 minutes at a constant heating temperature of about 200° F., the amount of release of the biologically active agent, e.g. povidone-iodine, can be controlled depending on not only the concentration of the biologically active agent present in the polymeric film, but also by varying the heating temperature with respect to the period of heating. The amount of the biologically active agent released, in the presence of a polar liquid, can be controlled in one or more layers of the polymeric film by heating each film at a different temperature for a different period of time with different concentrations of the biologically active agent. Therefore, in preparing surgeon's latex glove, from a plurality of polymeric films in accordance with this invention, each film of the glove can have a different concentration of the agent and be heated at a different temperature for a different period of time to obtain a plurality of polymeric films wherein each film releases the biologically active agent at a different rate based on the amount, i.e., concentration, of the biologically active agent, the temperature, and the period of heating each film.

The following examples illustrate the process of preparing the latex films capable of time-releasing the active agent in accordance with these aspects of the present invention.

Specifically, a surgeon's glove was prepared by dipping a hand form into a tank containing a freshly prepared mixture of one part by weight of a 10% povidone iodine solution and one part by weight of a synthetic latex. The form was removed from the tank and dried for about 40 minutes at 200° F. it was found that the amount of povidone-iodine released from the first layer of latex film into saline water, simulating moist skin, was about 3 micrograms/2 cc. Repeating the process, a second layer was applied and the form was dried for 20 minutes at 200° F. The second layer was found to release the povidone-iodine at 10 micrograms/2 cc. Thus, the first layer provides a more stable and longer term barrier film with respect to the penetration of bacteria or viruses. However, since the second outer layer of the glove will be exposed to a greater pathogenic environment, a greater amount of the viricidal agent will be released over a shorter period of time in comparison to the inside layer. Thus, by wearing a surgical glove impregnated with the biologically active agent taught by this invention, large quantities of the agent can be released rather quickly by having larger amount of the agent in the outer layers and by heating the latex for shorter periods of time or at a lower temperature.

Where it is necessary to provide viricidal protection to surgeons or other health care personnel over a longer period, a more stable outer layer can be prepared which will release the povidone-iodine more slowly in the presence of a polar liquid. Thus, the inside layer of the glove may comprise a polymeric film having a higher concentration of the agent and subjected to a different heating temperature during the preparation of the film. The inside layer is in contact with the skin and, hence, hand perspiration causes the skin to be bathed in the povidone-iodine. Consequently, if the glove were to be punctured by a surgical blade or needle, the puncturing object would, by necessity, carry some of the povidone-iodine into the open wound, thus providing some protection against accidental inoculation.

For example, surgical gloves comprising multilayers can be manufactured wherein each layer contains the same or a different amount of the povidone iodine. The rate of release can be controlled or timed by varying the heating or drying period and temperature following the dispersion of the agent in the latex. A laboratory technician working in a hazardous environment may accidentally cause penetration of both glove and skin and would benefit from a surgical latex glove comprising a triple layer, for example a slow release middle layer with two fast release outer and inner layer of latex. This type of glove would provide a more stable, slow-release middle layer with a faster release layer on both the exterior and interior of the glove.

EXAMPLE 8

As an illustration of stability of shelf life, a mixture of a 1:1 povidone-iodine solution and latex was prepared and heated for about 40 minutes and then formed into a film. These films were held for abut 18 months and compared to similarly prepared latex films recently manufactured, and it was found that the release rates of the latex films held for 18 months in Saran wrap were substantially the same as the release rates for the samples of the recently prepared films, thus indicating a long shelf life.

As indicated above, gloves made with natural latex rubber and povidone-iodine can also be dried at higher temperatures (200°-400°) for periods of around 20 to 25 minutes. Gloves made in this manner readily release povidone-iodine when in contact with a polar liquid. However, if longer periods of drying are used, for example greater than about 10 minutes, at the higher temperatures, little or no povidone-iodine exudes from the glove on contact with a polar liquid.

With the former case above, it appear that the rubber micelles quickly coalesce and therefore the iodine has difficulty in penetrating the rubber polymer matrix to react with the unsaturated bonds. However, paths are available for the povidone-iodine to exude to the surface. In the latter case, the povidone-iodine is quickly trapped and the paths blocked, and some iodine may also react with the polymer. The amount of povidone-iodine released is inversely proportional to the drying time. This aspect of the present invention is illustrated by Example 9 below.

EXAMPLE 9

Two latex films were formed from the mixtures prepared in accordance with Example 1 above using a mixture holding time of about 1 hour. One film was dried at 400° F. for 5 minutes and the other film was dried at the same temperature for 10 minutes. Both samples were wiped with moist towels. The first sample produced a brown color blotch characteristic of povidone-iodine while the second sample produced no color when wiped with a moist towel.

EXAMPLE 10

Films were formed from the mixture prepared in accordance with Example 1 using a holding time for the mixture of 24 hours. The films were dried in the conventional manner with air drying for 20 minutes. Very little or no povidone-iodine was detected when the films were in contact with a polar liquid. The dried films above were heated at 400° F. for 5 minutes, and the presence of free iodine was readily observed on the surface of the films when in contact with polar liquid. During the holding period of the above mixture, iodine added to the double bonds of the latex. This chemical reaction was then reversed by the post heat treatment of the iodopolymer. This would also be the case with any iodine substitution.

The aforementioned controlled release of the povidone-iodine from the latex may also be beneficially incorporated into durable medical equipment such as catheters. Interdwelling urinary catheters, in particular are frequent and life-threatening sources of bacterial infection. The usual sequence of urinary infection in cathetered patients is an irritation of the urethral mucosa with a secondary bacterial infection which can spread to the bladder and ascend to the the kidney via the ureters.

Figure 4:
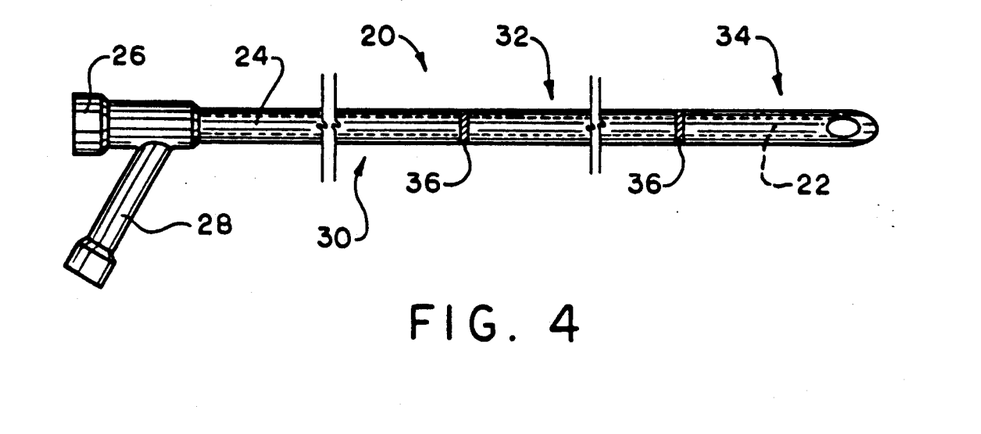
FIG. 4 is an elevational view of an interdwelling catheter in accordance with the invention.

The present invention can be utilized to provide catheters that have controlled release antimicrobial agents. For instance, the entire catheter may be conventionally molded from latex incorporating the antimicrobial agent. Alternatively, the catheter may be made with conventional materials and thereafter selectively or entirely coated with the antimicrobial substrate. Referring to FIG. 4 this is shown an interdwelling catheter 20, of the Foley type, which comprises an elongated tubular structure having a central passage 22 therein. The catheter 20 has a posterior section 24 located outside the patient. The section 24 includes a drainage section 26 adapted to be connected to a conventional receptacle for the receipt of urine and an injection section 28 for the delivery through the catheter passage 22 of medical solutions exiting at the anterior end at an opening. The catheter has three generally defined sections, 30, 32, 34, which may be coated or not coated with the same or different antimicrobial coatings. For indentification, the various sections may be identified by bands 36. Section 30 is located outside the patient and may or may not have antimicrobial properties as desired. Section 32 has a length generally coextensive with the urethral mucosa. Nothwithstanding the low patient toxicity to povidone-iodine, Section 32 is coated with a slow release substrate and preferably a coating without appreciable release formed in accordance with the process described above. In either case, the antimicrobial substrate is effective to prevent a nidus of infection while minimizing possible mucosal irritation. The section 34 is adapted to reside within the bladder and has a coating providing a slow, relatively high concentration release of povidone-iodine. The high concentration, slow release properties of this section continually sterilizes the urine, thus preventing an ascending infection from the bladder, to the ureter, and ultimately to the kidney. Thus, the multiple zone catheter interrupts the usual sequence of interdwelling infections.

In addition to the aforementioned controlled release of antimicrobial agent, it has been demonstrated that povidone-iodine is an effective curing agent for compounded or uncompounded latex at room temperature, and is further activated upon application of heat to the formed film. Unexpectedly, mixtures of natural latex rubber and povidone-iodine, without any vulcanizing agent, yield cast films which are vastly superior to cast films made from natural latex rubber without any vulcanizing agent or povidone iodine and comparable to films cast from mixtures of natural latex rubber and sulfur as the vulcanizing agent.

The excellent physical properties of the natural rubber latex and the povidone-iodine is due to the iodine functioning as a curing agent, initiating the polymerization of the double bonds of the natural rubber polymer and thereby cross linking the system. Only a very small amount of iodine free radicals need to be formed to cross link the polymer. While not wishing to be bound by any particular theory, it appears that the povidone-iodine in solution has available free iodine. The iodine is in constant equilibrium as follows:

$I_2 = 2I^{\bullet}$

Thus the free radical I° moiety can facilitate the cross linking of rubber polymers as described below:

$I_2 \rightarrow 2I^{\bullet}$

In addition to the above, the iodine adds to the unsaturated rubber to form the polyiodo derivative. However, this derivatization reaction is readily reversible and decomposes into iodine and the unsaturated moiety. Also, as the double bonds are cross linked they cease to be a scavenger of the povidone-iodine. These factors along with the stability of the povidone iodine complex account for the ability to control the release of povidone iodine to the surface of barrier articles by manipulating their manufacturing process variables.

This curing ability is demonstrated by the following example.

EXAMPLE 11

A 10% solution of povidone-iodine was admixed with an equal volume by weight of a natural, low ammonia latex emulsion, Hartex 104 manufactured by Firestone. The admixture was gently mixed until a uniform dispersion was achieved. The admixture was spread on a forming plate to a thickness of 10 mils and dried at 40° C. for a period of 20 minutes. The aforementioned latex emulsion is not compounded with any curing agents such as sulfur or other vulcanizing agents. The dried film latex substrate was stripped from the forming plate and cut into 2 inch by 2 inch samples.

Second, a natural, low ammonia latex emulsion, Hartex 104 manufactured by Firestone, was spread on a forming plate to a thickness of 10 mils and dried at 40° C. for a period of 20 minutes. The resulting dried film substrate was stripped from the forming plate and cut into 2 inch by 2 inch samples.

Third, a commercially available examination glove having a thickness of 10 mils was cut into 2 inch by 2 inch samples.

The three sets of samples were then subjected to elongation in both directions and to penetration by a sharp object. The povidone-iodine cured latex substrate and the examination glove were stretched to an elongation of 800%. Neither broke, ruptured or developed holes. The latex emulsion substrate without curing agent severed at about 200% elongation and intrasubstrate holes were noticed at an elongation of less than 50%.

A sample of each substrate was mounted about the periphery. An object with a sharp point was located at the center of each sample and deflected. A point penetrated the latex emulsion substrate without curing agent at less that ½ inch deflection. The povidone-iodine cured latex was penetrated by the point at 2 inch deflection. The examination glove was penetrated by the point at a 1.8 inch deflection.

The above clearly indicates that the povidone-iodine, in addition to the controlled release as an antimicrobial, can be used as a curing or vulcanizing agent for latex, in combination with or as replacement for current curing agents without a lessening of physical properties.

Various other embodiments and modifications of the above described embodiment will be apparent to those skilled in the art. Accordingly the scope of the invention is defined only by the accompanying claims.

The invention claimed is:

1. A polymeric film which control-releases a biologically active agent while in contact with a polar liquid to prevent the contamination and penetration of pathogens through said film, comprising: at least one layer of said polymeric film having dispersed therein povidone-iodine in the range of about 0.01% to 25% as said biologically active agent; said polymeric film prepared from a dispersion of said povidone-iodine and a film-forming polymeric material prepared by homopolymerization or copolymerization of ethylene monomers or monomers having at least two conjugated double bonds and capable of being vulcanized or cross-linked, said polymeric film being heated at elevated temperatures for a length of time varying with respect to the temperature and the amount of said povidone-iodine to control the release of said povidone-iodine from said film upon contact with said polar liquid.

2. The polymeric film as recited in claim 1 wherein said film-forming polymeric material is latex rubber.

3. The polymeric film as recited in claim 1 further characterized as comprising at least two layers of the polymeric film, one of said layers having a larger amount of povidone-iodine in comparison with the other layers.

4. The polymeric film as recited in claim 1 further characterized as comprising at least two layers of the polymeric film with about 0.01 to 10% by weight of povidone-iodine in each layer.

5. The polymeric film as recited in claim 4 wherein at least one of said layers of the polymeric film has dispersed therein a larger amount of povidone-iodine than the other layers.

6. The polymeric film as recited in claim 1 further characterized as comprising a plurality of layers of polymeric film at least one layer of said plurality of layers having dispersed therein a different amount of povidone-iodine and heated for a different length of time at a different temperature in comparison with the other layers.

7. A latex substrate comprising: a heat cured latex rubber having bonded thereto a predetermined amount of povidone-iodine substantially through van der Waals bonds by controlled heating thereby enabling local release of said povidone-iodine therefrom upon contact with a polar liquid, said predetermined amount being in the range of about 0.01% to 25%.

8. A latex substrate comprising: a film layer of cured latex rubber incorporating povidone-iodine therewithin formed from a mixture comprising said latex rubber and said povidone-iodine, said mixture being processed to a predetermined exclusion of covalent bonding between said latex rubber and said povidone-iodine, said povidone-iodine being present in the amount of about 0.1% to 10%.

9. A latex rubber substrate comprising: a latex rubber and an effective amount of povidone-iodine formed from a mixture comprising said latex and said povidone-iodine, said povidone-iodine being in the amount of about 0.01% to 25% and functioning as a vulcanizing and cross linking agent upon heating of said mixture at temperatures below about 400° to permit release of said povidone-iodine as an antimicrobial upon contact with a polar liquid.

10. A multilayer latex article comprising: a plurality of heat cured latex rubber substrate films, at least one of said films being a controlled release film having incorporated therewithin povidone-iodine in the range of about 0.01% to 25%, said povidone-iodine in said controlled release film having controlled van der Waals bonding with said latex.

* * * * *